(12) United States Patent
Henrotin et al.

(10) Patent No.: US 9,561,180 B2
(45) Date of Patent: *Feb. 7, 2017

(54) INTRA-ARTICULARLY SUPPLEMENTATION METHOD FOR TREATING JOINT DISEASES AND INJURIES

(71) Applicants: UNIVERSITE DE LIEGE, Angleur (BE); KITOZYME S.A., Herstal (BE)

(72) Inventors: Yves Henrotin, Beaufays (BE); Christelle Sanchez, Fraipont (BE); Frederic Oprenyeszk, Hermee (BE); Pierre Drion, Soiron (BE)

(73) Assignees: UNIVERSITE DE LIEGE, Angleur (BE); KITOZYME S.A., Herstal (BE)

( * ) Notice: Subject to any disclaimer, the term of this patent is extended or adjusted under 35 U.S.C. 154(b) by 39 days.

This patent is subject to a terminal disclaimer.

(21) Appl. No.: 14/541,540

(22) Filed: Nov. 14, 2014

(65) Prior Publication Data

US 2015/0072013 A1 Mar. 12, 2015

Related U.S. Application Data

(62) Division of application No. 13/581,376, filed as application No. PCT/EP2011/052020 on Feb. 11, 2011, now Pat. No. 8,889,158.

(30) Foreign Application Priority Data

Feb. 25, 2010 (EP) .................................... 10154712

(51) Int. Cl.
| | | |
|---|---|---|
| *A61K 9/00* | (2006.01) | |
| *A61K 31/722* | (2006.01) | |
| *A61K 31/734* | (2006.01) | |
| *A61K 9/06* | (2006.01) | |
| *A61L 27/20* | (2006.01) | |
| *A61L 27/26* | (2006.01) | |
| *A61L 27/38* | (2006.01) | |
| *A61L 27/52* | (2006.01) | |
| *A61K 9/14* | (2006.01) | |
| *A61K 45/06* | (2006.01) | |

(52) U.S. Cl.
CPC . *A61K 9/06* (2013.01); *A61K 9/14* (2013.01); *A61K 31/722* (2013.01); *A61K 31/734* (2013.01); *A61K 45/06* (2013.01); *A61L 27/20* (2013.01); *A61L 27/26* (2013.01); *A61L 27/3817* (2013.01); *A61L 27/52* (2013.01); *A61L 2430/06* (2013.01)

(58) Field of Classification Search
None
See application file for complete search history.

(56) References Cited

U.S. PATENT DOCUMENTS

| | | | | |
|---|---|---|---|---|
| 6,165,503 A | * | 12/2000 | Gaserod | B01J 13/02 424/451 |
| 2004/0047912 A1 | | 3/2004 | Bardonnet | |
| 2006/0029578 A1 | * | 2/2006 | Hoemann | A61K 31/727 424/93.7 |
| 2006/0280797 A1 | | 12/2006 | Shoichet | |

FOREIGN PATENT DOCUMENTS

WO 2007/135114 11/2007

OTHER PUBLICATIONS http://medical-dictionary.thefreedictionary.com/chitosan referenced on Feb. 17, 2016.*
R. Seda Tiğli et al., "Evaluation of alginate-chitosan semi IPNs as cartilage scaffolds," Journal of Materials Science: Materials in Medicine, 2009, Nov. 2008, vol. 20, No. 3, pp. 699-709.
Limor Baruch et al., "Alginate-Chitosan Complex Coacervation for Cell Encapsulation: Effect on Mechanical Properties and on Long-Term Viability," Biopolymers, 2006, vol. 82, pp. 570-579.

* cited by examiner

*Primary Examiner* — Jessica Worsham
(74) *Attorney, Agent, or Firm* — Jacobson Holman, PLLC.

(57) ABSTRACT

A hydrogel bead for intra-articular supplement made by:
providing a solution of alginate,
providing a solution with chitosan having a Mw between lower than 60 kD,
mixing the solution of alginate and the solution of chitosan, wherein the mixed solution comprises between 0.5 and 0.7% (w/v) of chitosan and between 1 and 1.4% alginate (w/v),
introducing droplets of the mixed solution into a solution with $Ca^{2+}$ or $Sr^{2+}$ cations and
isolating polymerised beads from the solution with cations.

11 Claims, 2 Drawing Sheets

INTRA-ARTICULARLY SUPPLEMENTATION METHOD FOR TREATING JOINT DISEASES AND INJURIES

FIELD OF THE INVENTION

The present invention relates to a method of producing spherical hydrogel beads comprising a mixture of chitosan and alginate.

The present invention also relates to a new supplementation method and composition for treating joint disorders, particularly osteoarthritis.

BACKGROUND OF THE INVENTION

Osteoarthritis (OA) is a progressive degenerative disorder accompanied by pain and characterized by a breakdown of cartilage in articular joints, a deterioration of the synovial fluid present in the articular joints, and a resulting osteosclerosis.

Osteoarthritis increases with age, with a probability higher than 60% of those 60 years old or older.

Today, to remediate to the mechanical pain accompanied with OA, the present therapy is generally, either therapeutic with administration of analgesic or anti-inflammatory agents or a surgical therapy with partial or total joint replacement. An alternative approach is viscosupplementation which is an injection into the joint of a biocompatible viscous (e.g. Hyaluronic acid) lubricant that reduces friction and pain.

Viscosupplementation is used to supplement synovial fluid that lubricates and protects the articular joints. Indeed, in OA patient, the synovial fluid is modified with a decrease of concentration and molecular weight (Mw) of hyaluronan (or salt of hyaluronic acid HA).

Intra-articular injections comprising high molecular weight of HA preparations are currently available and used to treat knee, hip, carpometacarpal joint of the thumb or ankle. These preparations require one (Durolane TM, Q-Med AB, Uppsala, Sweden), three (Synvisc®, high molecular weight cross-linked HA, Orthovisc®) to five (Hyalgan®, Supartz®) intra-articular (IA) injections (1 to 3 ml containing 5 to 20 mg/ml HA per injection according the joint).

TABLE 1

Hyaluronic acid (HA) preparations

| Trade name | Corporation | Average Mw (kD) |
|---|---|---|
| Synvisc ® (Hylan G-20) | Biomatrix (Canada) | 6.000-7.000 |
| Healon ® | Pharmacia/Upjohn (Sweden) | 1.900-3900 |
| Orthovisc ® | Anika (USA) | 1.700-2.900 |
| Arthrum ® | LCA (France) | 2.000 |
| Adant ® | Meiji Seika (Japan) | 900-1.200 |
| SupArtz ®, Artz ®, Artzal ® | Seikagaku (Japan) | 600-1.200 |
| Ostenil ® | Chemedica (France) | 1.200 |
| Hyalgan ® | Fidia (Italy) | 500-730 |
| Durolane ™ | Q-Med AB (Sweden) | ≥9000 |

HA preparations vary in a number of characteristics, including for example, the source of HA (animal-derived or bacterial), the concentration and Mw of HA and the type and degree of chemical crosslinking used, if any. Usually, most injectable HA preparations, once injected, have residence half-life between hours to several days.

Several studies have compared the efficacy of the above-mentioned products and differently concluded to a marked reduction of pain and improved function of patients with knee OA. Some concluded that at best there is small effect compared to placebo injection. Others observed that 3-5 weekly injections of one of the above products, significantly improved the pain and functional status of patients with OA and that, although the onset of improvement was delayed by 3-4 weeks, the effect can last at least six months and up after treatment cessation. Other observed beneficial effects on OA symptoms, not only for knee OA but also for ankle or carpometacarpal joint of the thumb OA, but also adverse effects.

Moreover, clinical effect may be rapid at 1 week and may last for six months or more, but in all cases, multiple injections are essential for a prolonged (six month to one year) effect on osteoarthritic pain primarily because of the short residence half-life of most HA preparations.

Endly, WO2007/135114 describes viscosupplementation with polysaccharides compositions of a mixture of alginate and chitosan without generating insoluble coacervates. Coacervates are due to the polycationic nature of chitosan that makes compatibility difficult with other polysaccharides such as hyaluronic acid (a polyanion) or alginate. According to WO2007/135114, precipitation/coarcervation of polysaccharides such as chitosan and alginate prevents any formulation thereof as an injectable composition.

In WO2007/135114 a composition with an aqueous mixture of chitosan of a high degree of derivatization of at least 40% and an alginate is therefore described as highly viscous without generating insoluble coacervates.

A continued need exists to develop new intra-articular supplement product that protect cartilage against mechanical strains, provide effective relief to OA patient without necessitating multiple injections and to avoid adverse effect.

We have now found a new method of producing a homogenous hydrogel matrix comprising alginate and chitosan wherein chitosan is of low molecular weight and coacervates. The resulting alginate/chitosan beads obtainable by the new method remain surprisingly homogenous and stable when used for intra-articularly supplementation.

We have now found a new method and composition for single intra-articular supplementation of chitosan/alginate beads with a long-term residence (at least two weeks) in the joint without increasing viscosity of the synovial fluid.

The foregoing summary and the following description are not restrictive of the invention as claimed.

SUMMARY OF THE INVENTION

One aspect of the present invention relates to a method of producing a hydrogel matrix comprising the steps of:
 providing a solution of alginate,
 providing a solution with chitosan having a Mw between lower than 60 kD,
 mixing the solution of alginate and the solution of chitosan, wherein the mixed solution comprises between 0.5 and 0.7% (w/v) of chitosan and between 1 and 1.4% alginate (w/v),
 introducing droplets of the mixed solution into a solution with $Ca^{2+}$ or $Sr^{2+}$ cations and
 isolating gellified beads from the solution with cations.

In certain embodiments of methods of the present invention, the droplets of the mixed solution are introduced in a solution of $Sr^{2+}$ ions.

In particular embodiments of this method the mixed solution comprises 0.6% chitosan and or comprises 1.2% alginate.

In particular embodiments of methods of the present invention the ratio between alginate and chitosan in the mixed solution is between 1.4 and 2.8, or between 1.75 and 2.25 or is about 2.

In particular embodiments of methods of the present invention the chitosan has a Mw of between 35 and 45 kD and/or is of animal or preferably of vegetable origin.

In other particular embodiments of methods of the present invention, the method further comprises the step of mixing the beads in a thermosensitive hydrogel. Herein the ratio between beads and hydrogel is for example between 5/1 and 1/1, or between 4/1 and 2/1.

In other particular embodiments of methods of the present invention the formation of beads is performed by passing droplets through a needle to obtain beads with a diameter between 0.01 and 5 mm.

Another aspect of the present invention refers to a spherical hydrogel bead comprising a homogeneous mixture of chitosan and alginate, wherein said bead is obtainable by the methods as described above.

Another aspect of the present invention refers to a spherical hydrogel bead with a diameter between 0.01 and 5 mm, comprising a homogeneous mixture of chitosan and alginate, characterised in that the bead comprises between 1 and 1.4% alginate and between 0.5 and 0.7% chitosan, for example, the bead comprises 1.2% alginate, or for example the bead comprises 0.6% chitosan.

In particular embodiments of beads of the present invention, the ratio of alginate/chitosan is between 1.4 and 2.8, preferably between 1.75 and 2.25, most preferably between 1.8 and 2.2.

In other particular embodiments of beads of the present invention the chitosan has a Mw between 35 and 45 kD and/or is of animal or vegetable origin.

The invention also relates to an intra-articular supplement comprising spherical hydrogel beads with a diameter between 0.01 and 5 mm, comprising a homogeneous mixture of alginate and chitosan of Mw lower than 60 kD, characterised in that said beads comprise between 1 and 1.4% alginate and between 0.5 and 0.7% chitosan.

The intra-articular supplement may further comprise a viscous thermogelling gel as for example a polysaccharide hydrogel, particularly a chitosan hydrogel.

By polysaccharides, one means biopolymers such as hyaluronic acid known as having repeating disaccharide units composed of glucuronic and N-acetyl-glucosamine, alginates and chitosan.

Chitosan is a polysaccharide widely available in nature obtained by chemical deacetylation of chitin and the principal constituent of crustacean exoskeletons but also from the mushrooms wall. It is composed of D-glucosamine units and N-acetyl-D-glucosamine units.

The intra-articular supplement may also comprise a component selected from the group consisting of non-steroidal anti-inflammatory drug, anaesthetic, opioid analgesics, corticosteroids, antineoplastic, monoclonal antibodies, chimeric monoclonal antibodies, vitamins, minerals, nutraceuticals.

The intra-articular supplement may also contain additional active or inactive components including for example, the non-steroidal anti-inflammatory drugs (NSAIDS) e.g. diclofenac™, ibuprofen™, piroxicam™; anesthetics, e.g. Lidocaine™ and Bupivacaine™; opiod analgesics, e.g. codeine and morphine; corticosteroids, e.g., dexamethasone and prednisone; antineoplastic agents such as Methotrexate™; anti-viral agents, e.g. Acyclovir™ and Vidarabine™; monoclonal antibodies e.g. Humira™ and chimeric monoclonal antibodies e.g. infliximab™. Intra-articular injectable supplements may also contain components such as cells, protein, DNA, minerals e.g. selenium, strontium, vitamins e.g. tocopherol, nutraceuticals e.g. curcumin or other desirable biologically active material.

The invention also relates to a supplementation method for treating joint disorder of a subject, and for reducing pain and discomfort associated with joint injury or joint diseases including osteoarthritis and traumatic cartilage lesions.

Example of such joint diseases include osteoarthritis (primary (idiopathic) or secondary), rheumatoid arthritis, joint injury (e.g. traumatic or repetitive motion injury), cartilage pathology (e.g. chondrocalconsis, chondromalacia), septic arthritis. The invention further provides methods of reducing pain associated with such diseases, to repair bone and cartilage lesion and to slow down disease progression.

The supplementation method of treating a joint disorder comprises administering an intra-articular supplement prepared according to the invention.

The supplementation method may comprise a single or multiple intra-articular injections or implantation of the supplement in an amount sufficient to provide a is therapeutic effect.

The intra-articular injection or implantation is done directly in bone and/or cartilage defect of human or non-human mammals for example by arthroscopy or with an injection device such as a syringe.

Examples of administration sites include the knee, shoulder, ankle, temporo-madibular and carpo-metacarpal joints, elbow, hip, wrist, intervertebral disc.

The invention further provides a supplementation device comprising a pre-filled, single use syringe having a single dose of the supplements.

Figure 1:
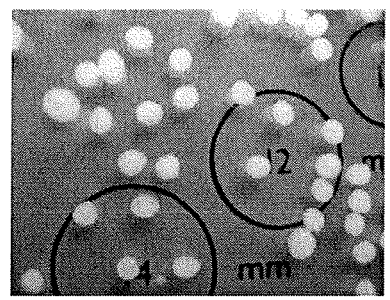
FIG. 1 shows beads obtained according to the method of the invention

A: Subchondral Bone; B: Cell-colonized hydrogel; C: cell colonized so Chitosan/alginate bead; D: Cell embedded in chitosan lacunae.

DETAILED DESCRIPTION OF THE INVENTION

One aspect of the present invention relates to a method of producing a hydrogel matrix. This method comprises the following steps:
providing a solution of alginate,
providing a solution of chitosan with a Mw lower than 60 kD, mixing the solution of alginate and the solution of chitosan, wherein the mixed solution comprises between 0.5 and 0.7% (w/v) of chitosan and between 1 and 1.4% alginate, introducing droplets of the mixed solution into a solution with $Ca^{2+}$ or $Sr^{2+}$ ions isolating gellified beads from the solution with cations.

The hydrogel which is obtained by this method results in a homogeneous matrix of calcium alginate and chitosan.

The matrix as obtained in the present invention differs from prior art matrices which have a core of one component, coated with a layer of another component.

The matrix as obtained in the present invention has the advantage that the porosity of the matrix can be more accurately defined compared to matrices which are first lyophilised to obtain a certain degree of porosity.

The matrix as obtained in the present invention has the advantage to be composed with a low molecular weight chitosan particularly between 15 and 50 kDA which spontaneously forms an homogenous network in the alginate matrix.

As indicated in the examples section, the alginate and chitosan which are used to prepare the hydrogels are dissolved in strong alkaline or acidic buffers which have a sterilising effect. This is an additional advantage of the present invention.

In the methods in accordance with the present invention the alginate and chitosan solutions can be mixed to obtain beads with different concentrations. Particular embodiments of the present invention relate to beads wherein the composition, prior to the gelification by calcium or strontium ions comprises 0.4, 0.45, 0.5, 0.55, 0.60, 0.65, 0.70, 0.75 or 0.80% (w/v) chitosan, and independently thereof comprises 0.9, 0.95, 0.1, 0.105, 0.11, 0.115, 0.12, 0.125, 0.13, 0.135, 0.14, 0.145 or 1.5% (w/v) alginate. In particular embodiments the concentration of chitosan ranges from 0.5 to 0.7%, or from 0.55 to 0.65%. In other particular embodiments the concentration of alginate ranges from 1. to 1.4% or from 1.25 to 1.35%. A particular embodiment of hydrogel comprises about 0.6% chitosan and about 1.2% alginate.

Further embodiments of methods and compositions of the present invention relate to hydrogel composition and beads obtained thereof wherein the ratio between alginate and chitosan in the mixed solution is between 1.4 and 2.8, more particularly between 1.5 and 2.7, more particularly between 1.6 and 2.6, or between 1.75 and 2.25. Particular values of this ratio are about 1.9, 1.95, 2.0, 2.05 and 1.

In the methods of the present invention the average size of the beads can be adapted and empirically determined by adjusting the diameter of the needle which is used to form the droplets which are introduced into the calcium or strontium solution. Envisaged herein are beads with a diameter between 0.01 and 5 mm. These dimensions provide a compromise between the ease of manipulation and the diffusion of nutrients into the beads.

The chitosan from the present invention may be isolated from different animal sources such as crustaceans (prawn shells) or squids. Alternatively the chitosan may be of vegetal, more of particularly fungal origin, such as Mucoralean strains, *Mucor racemosus* and *Cunninghamella elegans, Gongronella butleri, Aspergillus niger, Rhizopus oryzae, Lentinus edodes, Pleurotus sajo-caju, Zygosaccharomyces rouxii Candida albicans* or *Agaricus bisporus*.

Chitosan further exists in diverse types of molecular weight. Herein, the chain length of chitosan may contribute to the three dimensional structure of the hydrogels. Typical chitosans, for use in the present invention can have an average molecular weight between 15 and 50 kD, more particularly between 35 and 45 kD.

The method of manufacturing beads as described above, results in the formation of spherical hydrogel beads which comprise a homogeneous mixture of chitosan and alginate.

In particular embodiments, supplements are formulated as a biphasic supplement material formed by beads and a viscous gel. This supplement includes a polymeric matrix ("gel"), and the spherical three-dimensional beads comprising chitosan and alginate.

This allows to formulate an implantable or injectable gel which upon implantation, ensures an optimal space distribution in the host tissue or organ. The gel which is typically used herein in the supplement together with the beads prepared by the method of the invention, is a thermosensitive gel. These gels remain liquid at ambient temperature (in a device used for introduction in to the patient), but become solid upon introduction into the body at about 37° C. This in situ gelification maintains the beads in their spatial distribution. In vitro tests have demonstrated that beads were homogenously distributed in such a hydrogel when heated to 37° C. Examples of thermosensitive hydrogels include poly (N-isopropylacrylamide (PNIPAAm). A particular type hereof is chitosan.

Without being bound by theory it is believed that the chitosan network within the microbeads confers particular mechanical properties at the beads such that they are less compressible and more resistant to pressure than the beads made of alginate only. The matrices of the present invention provide inter-connected chitosan trabeculae within an alginate gel, resulting in an environment which is favourable for cellular culture by providing an aqueous medium with a neutral pH.

Such trabeculae are obtained by insoluble chitosan which forms coacervates which create a basket-like structure network or trabeculae when mixed with alginate. The trabeculae are of varying thickness and length and provide to the beads particular biological and mechanical properties such as phenotype stabilisation, deformability, elasticity and compressive modulus.

EXAMPLES

Example 1

Preparation of Alginate/Chitosan Beads

Figure 2:
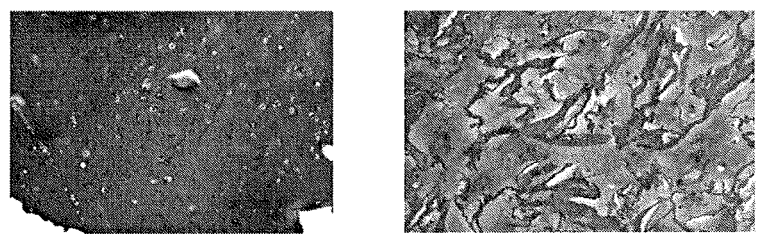
FIG. 2 shows a section of an alginate bead (A) and a chitosan/alginate bead (B) [chitosan: dark grey trabeculae; alginate: light grey background].
Figure 3:
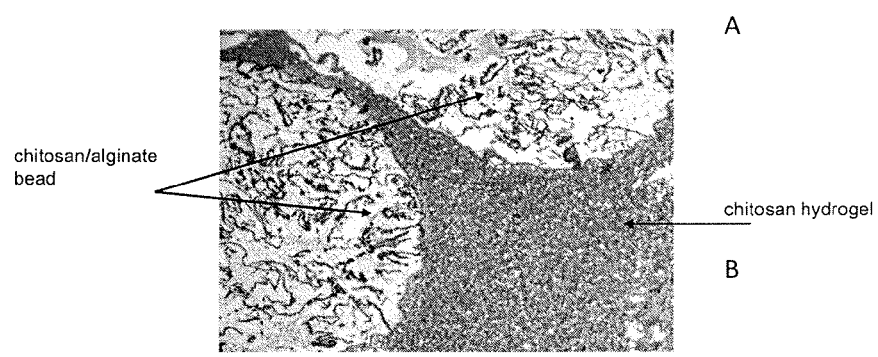
FIG. 3 shows at low magnification chitosan/alginate beads embedded in a chitosan hydrogel.

Beads are prepared from a homogeneous mixture of chitosan (0.6% final) and alginate (1.2% final). The two solutions are prepared separately before being mixed. The solutions of alginate and chitosan are prepared in the following way: An alginate solution 2.4% (W/v) in 0.16 M NaOH and a solution of chitosan 1.333% (w/v) in 1.666 M HAc are prepared. To 10 volumes of the alginate solution, 1 volume of a 1 M Hepes (4-(2-hydroxyethyl)-1-piperazineethanesulfonic acid) solution is added. After homogenization, 9 volumes of chitosan solution are progressively added, while mixing regularly and vigorously. The chitosan/alginate solution is slowly passed through a 25 gauges needle in a dropwise fashion into a 102 mM $CaCl_2$ solution (Sigma-Aldrich, Bornem, Belgium). After instantaneous gelation, the beads are allowed to gellify further for 10 min in this $CaCl_2$ solution. At microscopic scale, the chitosan (stained in red by the eosin) forms a basket-like structure, composed of trabeculae or fibres of varying thickness and length (see FIGS. 2 and 3). The interstices herein are filled by alginate (hematoxylin stained in violet).

Example 2

Formulation of Beads in a Thermosensitive Hydrogel

The beads are mixed with a vegetable (*Agaricus bisporus*) chitosan hydrogel (Kitozyme, Alleur, Belgium). This step is performed below 27° C. to avoid hydrogel gelification. A ratio of beads/hydrogel of 3/1 (v/v) has been used.

Example 3

Implantation in an Animal Model

Figure 4:
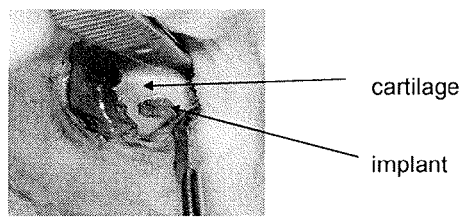
FIG. 4 shows the implantation of a thermosensitive chitosan hydrogel comprising 0.6% chitosan/1.2% alginate beads (*A. bisporus* chitosan (40 kD))

A gel as described under example 2, has been implanted in a rabbit with subchondral bone and cartilage defect joint. (FIG. 4).

Figure 5:
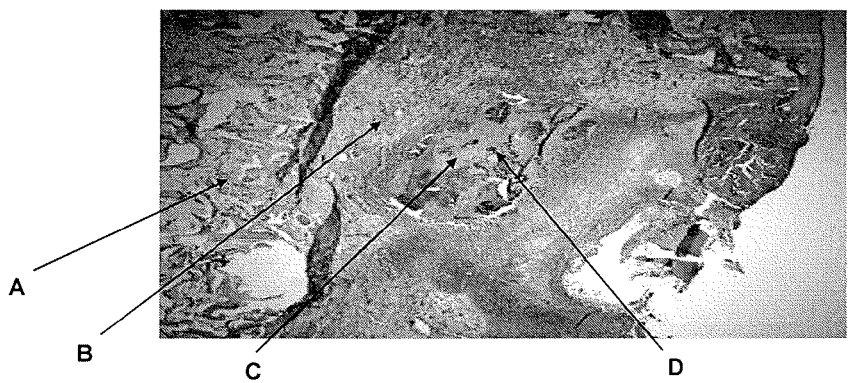
FIG. 5 shows the histological evaluation of the implant 15 days after implantation.

After 15 days of implantation, the implant was evaluated (FIG. 5). The lesion remains filled with the implant. Beads and viscous hydrogel remain constant at least two weeks after injection in the injured joint, while maintaining a safety profile.

Further it is observed that the implant is colonised with cells originating from the underlying bone marrow. Cells were encountered in the settled thermosensitive chitosan hydrogel (B) as well as in the chitosan alginate beads (C) (chitosan trabeculae are indicated by D). This test confirms that the biphasic implant can be easily handled and grafted. The biodegradable nature of the implant ensures a progressively resorption after implantation.

Example 4

Effect of Chitosan Molecular Weight In Beads Formation

Different molecular weights of native chitosan have been used in the process according to the invention. Different physical parameters such as pH and viscosity of the mixed solution (with chondrocytes were measured., Osmolarity of the resulting hydrogel is measured according to a well-known technique in the art.

TABLE 1

| Solutions | pH | Viscosity (Cps) | Osmolarity (mOsm/kg) |
|---|---|---|---|
| Alginate 1.2%/chitosan 22 kDa 0.6% | 7.8 | 110.7 | 324 |
| Alginate 1.2%/chitosan 30 kDa 0.6% | 8.3 | 230 | 305 |
| Alginate 1.2%/chitosan 32 kDa 0.6% | 7.8 | 192 | 308 |
| Alginate 1.2%/chitosan 55 kDa 0.6% | 8.0 | 279 | 290 |
| Alginate 1.2%/chitosan 55 kDa 0.6% | 8.2 | 336 | 302 |
| Alginate 1.2%/chitosan 91 kDa 0.6% | | Impossible to mix | |
| Alginate 1.2%/chitosan 146 kDa 0.6% | | Impossible to mix | |

We concluded that mixed beads can be made with native chitosan below 55 kDa. For example, at 91 kDA, beads cannot be made using the process described in our invention and at the ratio alginate 1.2% and chitosan 0.6%, the chitosan solution is too viscous. Therefore, the selection of chitosan molecular weight is an essential element in our invention.

Example 5

A Supplementation Method for Treating an Articular Joint of a Human Subject or an Animal with a Needle A needle has been used to deliver the intra-articularly supplement. For intra-articular administration, supplement is delivered in the synovial cavity at a density of 1,000 to 20,000 beads of 0.1 to 0.5 μm per ml in a volume of approximately 1-2 ml per injection. For example, 1 ml of physiological liquid containing 10,000 beads of 0,2 μm is injected into a knee joint using a fine (e.g. 14-22 gauge, preferably 18-22 gauges) needle.

Example 6

A Supplementation Method for Treating an Articular Joint of a Human Subject or an Animal with a Trochar A trochar has been used to deliver the supplement in the small to medium iv cartilage defect (less than 1 cm$^2$). For implantation, supplement is delivered in the cartilage through the trochar at a density of 5 to 50 beads of 1 to 5 mm diameter. For example, 4 beads of 1 mm diameter are implanted in a traumatic cartilage lesion of 0.5 cm diameter and 1 mm depth diameter.

The invention claimed is:

1. A spherical hydrogel bead with a diameter between 0.01 and 5 mm, comprising a homogeneous mixture of alginate and native chitosan of Mw between 22 kD to 55 kD, characterised in that said bead comprises between 1% (w/v) and 1.4% (w/v) alginate and between 0.5% (w/v) and 0.7% (w/v) native-chitosan, wherein the hydrogel bead comprises inter-connected chitosan trabeculae within an alginate gel.

2. The bead according to claim 1, wherein said bead comprises 1.2% (w/v) alginate.

3. The bead according to claim 1, wherein said bead comprises 0.6% (w/v) native chitosan.

4. The bead according to claim 1, wherein the native chitosan has a Mw between 35 and 45 kD.

5. An intra-articular supplement comprising spherical hydrogel beads with a diameter between 0.01 and 5 mm, comprising a homogeneous mixture of alginate and native chitosan of Mw between 22 kD to 55 kD, characterised in that said beads comprise between 1% (w/v) and 1.4% (w/v) alginate and between 0.5% (w/v) and 0.7% (w/v) native chitosan, wherein the hydrogel beads comprise inter-connected chitosan trabeculae within an alginate gel.

6. The intra-articular supplement according to claim 5 further comprising a viscous thermogelling gel.

7. The intra-articular supplement according to claim 5 wherein the native chitosan is of animal or vegetal origin.

8. The intra-articular supplement according to claim 5 further comprising a component selected from the group consisting of non-steroidal anti-inflammatory drug, anaesthetic, opioid analgesics, corticosteroids, antineoplastic, monoclonal antibodies, chimeric monoclonal antibodies, vitamins, minerals, and nutraceuticals.

9. A supplementation method for treating an articular joint of a human subject or an animal, the method comprising a single or multiple intra-articular administration of hydrogel beads according to claim 1.

10. A supplementation device containing the hydrogel beads according to claim 1.

11. The intra-articular supplement according to claim 6, wherein the viscous thermogening gel is a chitosan hydrogel.

\* \* \* \* \*

UNITED STATES PATENT AND TRADEMARK OFFICE
CERTIFICATE OF CORRECTION

PATENT NO. : 9,561,180 B2  
APPLICATION NO. : 14/541540  
DATED : February 7, 2017  
INVENTOR(S) : Yves Henrotin et al.

Page 1 of 1

It is certified that error appears in the above-identified patent and that said Letters Patent is hereby corrected as shown below:

In the Specification

In Column 4, Line 27, please remove the word --is--.
In Column 4, Line 56, please remove the word --so--.
In Column 8, Line 23, please remove the word --iv--.

In the Claims

In Claim 11, Column 9, Line 2, please correct the spelling of --thermogening-- to --thermogelling--.

Signed and Sealed this
Eleventh Day of April, 2017

Michelle K. Lee
*Director of the United States Patent and Trademark Office*